US009149651B2

(12) United States Patent
Keltner et al.

(10) Patent No.: US 9,149,651 B2
(45) Date of Patent: Oct. 6, 2015

(54) NON-INVASIVE VASCULAR TREATMENT SYSTEMS, DEVICES, AND METHODS OF USING THE SAME

(75) Inventors: Llew Keltner, Portland, OR (US);
James C. Chen, Clyde Hill, WA (US)

(73) Assignee: PURDUE PHARMACEUTICAL PRODUCTS L.P., Stamford, CT (US)

( * ) Notice: Subject to any disclaimer, the term of this patent is extended or adjusted under 35 U.S.C. 154(b) by 1666 days.

(21) Appl. No.: 12/522,375

(22) PCT Filed: Jan. 8, 2008

(86) PCT No.: PCT/US2008/050544
§ 371 (c)(1),
(2), (4) Date: Jan. 4, 2010

(87) PCT Pub. No.: WO2008/086375
PCT Pub. Date: Jul. 17, 2008

(65) Prior Publication Data
US 2010/0121252 A1    May 13, 2010

Related U.S. Application Data

(60) Provisional application No. 60/879,508, filed on Jan. 8, 2007.

(51) Int. Cl.
*A61N 1/30* (2006.01)
*A61N 5/06* (2006.01)
*A61B 18/20* (2006.01)
*A61B 18/00* (2006.01)
*A61B 19/00* (2006.01)

(52) U.S. Cl.
CPC ............... *A61N 5/062* (2013.01); *A61B 18/203* (2013.01); *A61B 2018/0047* (2013.01); *A61B 2018/00452* (2013.01); *A61B 2019/409* (2013.01); *A61B 2019/4036* (2013.01); *A61N 5/0616* (2013.01); *A61N 2005/0645* (2013.01); *A61N 2005/0652* (2013.01)

(58) Field of Classification Search
CPC ............................ A61N 5/0616; A61N 5/062
USPC .................... 604/20, 500–522; 606/9; 607/94
See application file for complete search history.

(56) References Cited

U.S. PATENT DOCUMENTS

| | | | |
|---|---|---|---|
| 5,171,749 A * | 12/1992 | Levy et al. | 514/410 |
| 5,698,866 A | 12/1997 | Doiron et al. | |
| 5,944,748 A | 8/1999 | Mager et al. | |
| 6,096,066 A | 8/2000 | Chen et al. | |
| 6,445,011 B1 | 9/2002 | Hirano et al. | |
| 6,661,167 B2 | 12/2003 | Eliashevich et al. | |
| 6,784,460 B2 | 8/2004 | Ng et al. | |
| 6,958,498 B2 | 10/2005 | Shelton et al. | |
| 2005/0143793 A1 * | 6/2005 | Korman et al. | 607/94 |
| 2005/0228260 A1 | 10/2005 | Burwell et al. | |
| 2006/0276859 A1 | 12/2006 | Ferren et al. | |

FOREIGN PATENT DOCUMENTS

| WO | 02/041364 | 8/2002 |
|---|---|---|
| WO | 2006/031934 | 3/2006 |

* cited by examiner

*Primary Examiner* — Phillip Gray
(74) *Attorney, Agent, or Firm* — Troutman Sanders LLP

(57) ABSTRACT

An energy treatment system to treat a patient includes an energy delivery device having a plurality of energy emitters used in combination with an energy activatable drug. A mask can be used to define a treatment area. Energy from the energy emitters passes through an optical window of the mask to activate a cosmetically and/or therapeutically effective amount of the activatable drug at the target site to bring about a desired change of tissue, for example, to reduce visibility of one or more blood vessels, while energy from the energy emitters directed outside of the target site is blocked by the mask.

22 Claims, 13 Drawing Sheets

NON-INVASIVE VASCULAR TREATMENT SYSTEMS, DEVICES, AND METHODS OF USING THE SAME

CROSS-REFERENCE TO RELATED APPLICATION

This application is the National Stage of International Application No. PCT/US2008/050544, filed Jan. 8, 2008 and published as WO 2008/086375 on Jul. 17, 2008. The International Application claims the benefit under 35 U.S.C. §119 (e) of U.S. Provisional Patent Application No. 60/879,508 filed Jan. 8, 2007, which provisional application is incorporated herein by reference in its entirety.

BACKGROUND

1. Technical Field

The present invention relates to treatment systems and methods of treating a subject. In particular, the present invention provides systems and methods for using energy to provide non-invasive localized therapeutic and/or cosmetic treatments.

2. Description of the Related Art

Many types of vascular diseases, disorders, and conditions may be unsightly and/or uncomfortable. Spider veins are one type of vascular disease involving enlarged blood vessels similar to, but smaller than, varicose veins. Spider veins are often closer to the surface of the skin than varicose veins and may be highly visible. Short jagged vessels in a network of spider veins may look like tree branches or spider webs and can be found on various parts of the body, such as the legs and face. In some instances, spider veins may not cause any problems or symptoms and, consequently, may be treated solely for cosmetic reasons. In other circumstances, however, various unwanted symptoms may be associated with spider veins, including discomfort.

Currently, sclerotherapy can be performed to close the network of spider veins. In sclerotherapy, a solution is injected directly into the spider veins, and the solution causes the walls of the veins to swell, stick together, and seal shut. The tissue of the closed blood vessels then turns into scar tissue and is broken down by the subject's body. After a few weeks, the treated blood vessels may become less visible and, in some circumstances, may not be visibly distinguishable from the surrounding tissue, thereby improving the appearance of the subject's skin. Sclerotherapy is not always effective, however, in that it may be difficult to inject the solution directly into the relatively small spider veins.

Laser systems are also used to treat spider veins. Unfortunately, traditional laser systems employ expensive, bulky lasers that produce a narrow coherent laser beam unsuitable for simultaneously treating an entire network of spider veins. It may be particularly difficult to treat a network that spreads out over a large area because each branching section of the network has to be treated. Additionally, treating small blood vessels with a single laser beam may cause excessive, unwanted trauma to nearby tissue.

Varicose veins are abnormally enlarged blood vessels that result when veins have improperly functioning venous valves. The venous valves allow blood to flow in a retrograde, or reflux, direction. Superficial venous reflux introduces elevated intravascular pressure into veins that are intended to function at a relatively low pressure. This abnormally high pressure progressively promotes vein distention, dilation, and tortuosity. Because the superficial veins lack adequate muscle support and reside near the surface of the skin, they may become more visible with increased intravascular pressure. The condition is often further aggravated by the weakening of the affected vein's walls. Varicose veins are often in the back of the calf or on the inside of the leg between the groin and ankle. Invasive, surgical procedures are often performed to remove sections of the varicose veins. These invasive procedures may result in significant discomfort and trauma to adjacent tissues resulting in significant recovery periods.

BRIEF SUMMARY

Disclosed embodiments are related to non-invasive cosmetic and therapeutic systems. The methods, in some embodiments, include delivering a photoreactive agent to a target site. The target site is then illuminated with light having a waveband that overlaps with at least one absorption peak of the photoreactive agent until achieving a desired cosmetic effect, therapeutic effect, and/or other type of desired effect. The methods can be performed on different types of target sites having a wide range of sizes, and may be tailored using one or more parameters based on the diagnosis of the subject.

The target site may include unwanted tissue, such as aesthetically unattractive anatomical structures, visible blood vessels, skin abnormalities, discolorations, cancerous cells, skin markings (e.g., tattoos), and other unwanted features. Unattractive anatomical structures may be spider veins, varicose veins, and the like. Light therapy can destroy, damage, or otherwise treat these types of target sites. In some embodiments, for example, light is delivered to alter the appearance of skin abnormalities, such as naevus flammeus or a network of spider veins.

The system for performing the methods can include an external flexible patch and a container holding an activatable drug (e.g., a photoreactive agent). The patch, in some embodiments, includes a plurality of light emitters operable to excite the photoreactive agent. The patch can conform to a portion of a patient's body to position the light emitters with respect to an internal target site. The light emitters can produce a field of light that substantially matches the configuration of the target site, thereby treating the target site and limiting the treatment of nearby untargeted tissue. In this manner, an entire network of blood vessels, or a portion thereof, can be treated at the same time.

The patch may be single-use or multi-use. A disposable single-use patch may include a non-rechargeable power supply that provides sufficient power for a single treatment. A multi-use patch may include a rechargeable power supply or may be adapted to receive power from an external power supply, such as an electrical outlet.

In some embodiments, the patch has a relatively thin cross-sectional profile and is flexible to conform to irregular physical contours of a patient's body. The patch itself can receive power and then use that power to generate and emit light. In some embodiments, the patch has a thickness that is equal to or less than 50%, 40%, 20%, or 10% of a maximum transverse width of the patch. For example, if the patch has a generally circular shape as viewed from above, the patch can have a thickness that is equal to or less than about 10% of the diameter of the patch.

The patch can have an adhesive layer for coupling to a patient's body. When the patch is placed on the patient's body, a mask can be positioned relative to the patch so as to protect untargeted tissue. The mask, for example, can be sandwiched between the patch and the patient. An optical window in the mask allows illumination of only a certain region or site, such as the targeted site. The mask can be integrated into the patch.

In some embodiments, for example, the mask is in the form of a protective layer (e.g., a reflective layer or absorbing layer) integrated into the patch such that the mask is fixedly coupled between the light emitters and the targeted site. The mask, in some embodiments, can be made of a variety of materials, e.g., a Mylar film, an opaque material, an absorptive material, and the like, suitable for shielding tissue from the emitted energy.

In some embodiments, an addressable array of light emitters of a patch illuminates only an area of interest, thereby sparing non-targeted tissue. A single patch can therefore treat a wide range of treatment sites having different configurations and sizes. The patch can be conveniently programmed for a particular treatment. The addressable array of light emitters can be used, alone or in combination, with a mask.

Another way of protecting non-targeted tissue is to apply a spreadable protective substance (e.g., a protective cream or gel) directly onto the subject's skin. A physician visually inspects the applied protective substance to determine whether non-targeted tissue is properly shielded. In some embodiments, the protective substance can be used to trace the targeted site. In this manner, a user can conveniently form an envelope surrounding the targeted site. The patch, in some embodiments, is then applied to the subject such that the protective substance is sandwiched between the patch and the subject. Energy from the patch passes only through the optical window defined by the protective substance. After the treatment, the spreadable protective substance can be simply wiped off of the subject.

In some embodiments, a patch for delivering light includes a flexible substrate, a plurality of light emitters mounted to the flexible substrate, and a protective layer. The protective layer is sized and configured to protect tissue near the target site. The protective layer can have an optical window for mating with the target site and positioned with respect to the plurality of light emitters such that at least a portion of the light emitted from the plurality of light emitters passes through the optical window to the target site.

A flexible patch, in some embodiments, can carry a control assembly that turns light emitters "OFF" at the end of the treatment period. The control assembly may include an embedded timer. A power supply can be also embedded in the patch such that the power supply and light emitters are wholly contained in the patch.

Various types of photoreactive agents can be delivered to the target site. The photoreactive agent, when activated, damages, kills, induces cell apoptosis, induces tissue necrosis, or otherwise elicits a desired response of the targeted site. In one embodiment, the photoreactive agent binds to an endothelial surface of a vessel wall, and the agent is then activated. In one embodiment, the photoreactive agent is talaporfin sodium.

In some embodiments, a system and a method for treating blood vessels, e.g., spider veins, comprises administering a photoreactive agent to blood vessels that form the spider veins. A light source is positioned with respect to the blood vessels, such that light administered from the light source reaches the blood vessels to excite the photoreactive agent. The activated photoreactive agent causes a reduction in the visibility of the spider veins.

In some embodiments, an external device is adapted to be placed over tissue at or overlying a target site to be treated. A light emitter is physically coupled to the external device such that light outputted by the light emitter is emitted towards the target site, when the light emitter is activated and the delivery device lies closely against the tissue at or overlying the target site. A substantial portion of the light outputted from the light emitter is delivered outward from a longitudinal side of the external device facing the target site. In some embodiments, a majority of the light reaches the target site.

The external device can be used to adjust one or more characteristics, e.g., optical or physical characteristics, of targeted features. Such optical characteristics include, without limitation, color and visibility, as well as other characteristics that may impact the overall appearance of the subject. In some embodiments, the external device diminishes the color and/or visibility of a group of vessels.

In some embodiments, the external device can alter one or more physical characteristics of one or more anatomical features. Example physical characteristics include, without limitation, dimensions and shapes of the anatomical features. The external device can be used to cosmetically treat a wide range of vessels, including extremely small blood vessels that may be barely visible. Particularly, such small vessels may not result in any therapeutic problems and, consequently, may be treated solely for cosmetic reasons in spas, salons, skin care centers, clinics, and the like. Estheticians or beauticians can use the external device to improve the aesthetic appearance of the subject. The output of the external device can be adapted to prevent any therapeutic effects.

In some embodiments, an external device for treating a target site includes at least one light emitter operable to emit energy adapted to activate a drug at the target site of a subject. The external device also includes a mask that has an energy blocking portion and an optical window. The optical window is at least partially surrounded by the energy blocking portion.

In some embodiments, the optical window is positioned with respect to the at least one energy emitter such that emitted energy from the at least one energy emitter passes through the optical window and activates an effective amount (e.g., a cosmetically or therapeutically effective amount) of the drug at the target site so as to reduce visibility of one or more blood vessels at the target site, while at least some of the emitted energy from the at least one energy emitter is at least partially blocked by the energy blocking portion. In some embodiments, the energy activates a cosmetically effect amount of the drug. In some embodiments, the energy activates a therapeutically effect amount of the drug. The one or more blood vessels can be visible. For example, a network of blood vessels can form visible spider veins near the surface of the subject's skin. A single enlarged varicose vein may cause the subject's skin to protrude.

In some embodiments, a light treatment system for delivering light to a target site of a subject comprises a patch. The patch can include a substrate, a plurality of emitters coupled to the substrate, and a mask. The mask can be dimensioned and adapted to protect tissue beneath its lower surface. In some embodiments, the mask has an optical window corresponding to the target site and positioned with respect to the plurality of light emitters such that light emitted by the plurality of light emitters is operable to activate a photoreactive agent at the target site when the plurality of light emitters is energized. In some embodiments, packaging surrounds the patch and a dosage of a photoreactive agent. The packaging can be adapted to maintain the sterility of the patch and a container holding the dosage.

In some embodiments, a system for performing light treatment on a subject includes an external patch and a control assembly. The external patch includes a plurality of light emitters operable to generate a maximum illumination field of light. The control assembly includes a user input device. In some embodiments, the control assembly is operable to energize only a portion of the plurality of light emitters so as to produce a treatment illumination field of light that is smaller than the maximum illumination field of light. In some embodiments, the treatment illumination field of light substantially matches a shape of a target site based, at least in part, on at least one parameter inputted using the user input device. The user can input capture images, tracings, dimensions, and other parameters used to develop an appropriate treatment. In some embodiments, the treatment illumination field of light and the target site can have complementary shapes.

One method of treating an internal target site of a subject includes delivering a photoreactive agent to the target site having a visible network of spider veins. At least one light emitter can be positioned external to the subject and within optical range of the target site. Light is delivered from the at least one light emitter, positioned external to the subject, towards the target site to activate the photoreactive agent to reduce or eliminate the visibility of the network of spider veins. Energy treatment systems disclosed herein can be configured to perform such methods.

In yet other embodiments, a system and a method for performing light treatment on a subject include positioning an external mask on a subject to align an optical window in the mask with a target site. Light is delivered from a light emitter through the optical window to tissue at the target site sensitized with a photoreactive agent. Light can be delivered while the mask substantially prevents any emitted light from reaching tissue that contacts a lower surface of the mask. Energy treatment systems disclosed herein can be configured to perform such methods. The light can cause a cosmetic alteration of the target site without therapeutic alteration of the target site.

The treated vessel may be physically compressed using standard compression procedures after or during light activation. The compression may be provided, e.g., by a light emitting pressure anvil or roller that will provide activation and compression concurrently. The compression can facilitate destruction of the vessel.

Treatment parameters for energy treatment systems can be selected based on the diagnosis of the subject, and may include, without limitation, power density, treatment type, treatment duration or period, depth of penetration, pulse intensity, pulse duration, pulse repetition rate, stop-start time, position of an energy delivery device, and the like. Additional treatment parameters can also be used.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

In the following detailed description, certain specific details are set forth in order to provide a thorough understanding of various disclosed embodiments. However, one skilled in the relevant art will recognize that embodiments may be practiced without one or more of these specific details, or with other methods, components, agents, materials, etc. In other instances, well-known structures associated with energy delivery devices, control systems, patches, circuits, power regulators, and/or energy emitters have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

As used in this specification and the appended claims, the singular forms "a," "an," and "the" include plural referents unless the context clearly dictates otherwise. Thus, for example, reference to a patch including "an energy emitter" includes a single energy emitter, or two or more energy emitters. It should also be noted that the term "or" is generally employed in its sense including "and/or" unless the context clearly dictates otherwise.

As used herein, the term "energy treatment" is broadly construed to include, but is not limited to, delivering energy to ablate, destroy, damage, induce apoptosis, and/or induce necrosis. The energy treatment systems disclosed herein can treat target sites at different depths and positions in the subject's body. The treatment sites can include, without limitation, a region of a subject that contains unwanted anatomical structures, such as visible blood vessels, spider veins, skin abnormalities, discolorations, cancerous cells, skin markings (e.g., tattoos), and other unwanted features. Energy treatments include, without limitation, cosmetic treatments, therapeutic treatments, and other types of treatments.

Spider veins are especially well suited for energy treatments. The term "spider veins" is broadly construed to include, without limitation, telangiectasis, sunburst varicosities, naevus flammeus, naevus simplex, and other networks of permanently dilated vessels (e.g., capillaries, arterioles, and venules), such as relatively small vessels having average diameters equal to or less than about 5 mm. Spider veins may be permanently dilated capillary vessels proximate the surface of the skin in the face (e.g., near the nose, cheek, and/or chin), legs (e.g., upper thigh, below the knee joint, and around the ankles), and other locations.

Figure 1:
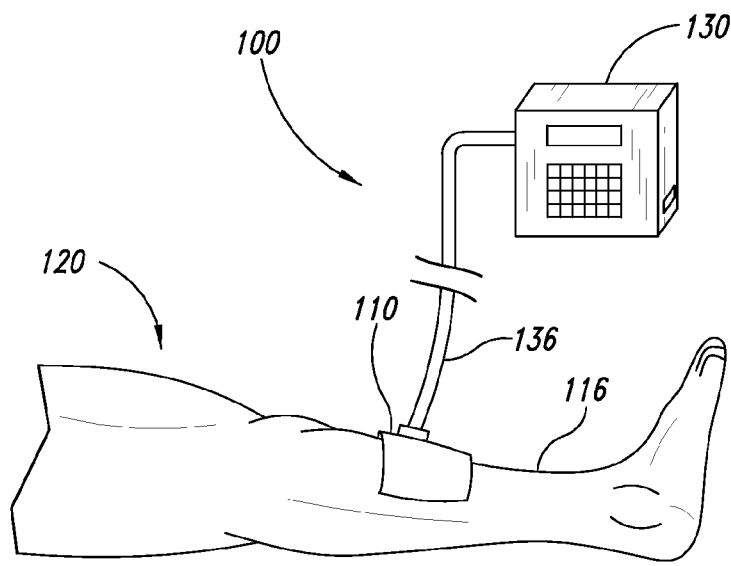
FIG. 1 is an elevational side view of a subject and an energy treatment system to deliver energy to the subject, according to one illustrated embodiment.

FIG. 1 shows an energy treatment system 100 including a conformable external delivery device 110 applied to a leg 116 of a subject 120, a control assembly 130, and a connector 136 extending between the delivery device 110 and the control assembly 130. The control assembly 130 delivers power to the delivery device 110 via the connector 136. The delivery device 110 is capable of delivering energy to various types of specifically targeted anatomical features suitable for undergoing energy treatment. Example anatomical features include, but are not limited to, tissue, organs, systems, and the like.

The delivery device 110 of FIG. 1 can output energy that, alone or in combination with a photoreactive agent, elicits a desired response to therapeutically alter or cosmetically alter, or both, one or more anatomical features of interest. Energy (represented by arrows in FIG. 2) outputted from the delivery device 110 is transdermally delivered into the subject 120. The subject 120 can be any host or animal (e.g., a mammal such as a human).

Unlike prior art procedures, the delivery device 110 treats specific tissue without using complicated processes for injecting solutions at precise locations which may be necessary for proper vessel closure. In sclerotherapy, for example, because the dimensions of spider veins are extremely small, it is difficult to inject a sufficient amount of the treatment solution into the spider veins. By contrast, the energy treatment system 100 can be quickly and accurately aligned with the treatment site and can then be activated to treat a relatively large treatment site without many of the unwanted complications associated with traditional sclerotherapy. The energy delivery device 110 can non-invasively deliver energy to minimize or limit trauma to the subject 120, to reduce the risk of infection, and to reduce recovery periods.

In some embodiments, an amount (e.g., a cosmetically effective amount, therapeutically effective amount, and the like) of light emitted from the delivery device 110 is used to affect (e.g., photo-activate or photo-excite) one or more target sites by subjecting the one or more target sites to one or more wavelengths of light that are approximately close to, if not equivalent to, at least one excitation wavelength of the cells at the target site. Energy treatments can be used to treat various types of conditions, diseases, symptoms, and/or problems to, for example, slow or limit the progression of the conditions, diseases, problems, reduce or eliminate the visibility of anatomical features, minimize unwanted symptoms, and the like. The power density in the targeted tissue can be maintained at or above a threshold level known to have beneficial responses at the target site. Threshold levels can vary for different types of tissues to account for properties (e.g., optical properties) of the tissues.

Figure 2:
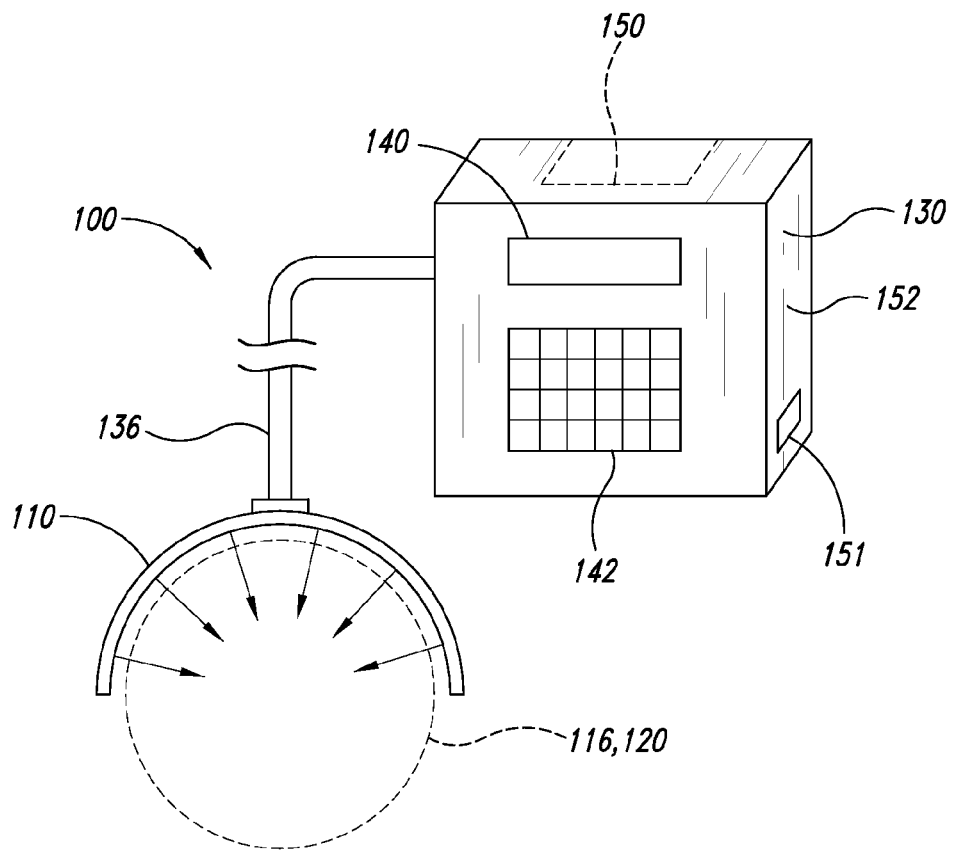
FIG. 2 shows an energy delivery device delivering energy to a treatment site of a subject, according to one illustrated embodiment.

The control assembly 130 of FIGS. 1 and 2 can be used to set the treatment parameters based, at least in part, on dimensions or measurements, captured images, scans, and/or other measurable criteria associated with a target site. Additionally, user feedback (e.g., a level of pain or discomfort) can be used to optimize and develop an interactive treatment plan. The appropriate light dosages can also be determined using clinical variables, such as visibility of features of interest, measurements of skin color, depth of the target sites, composition of tissue (e.g., fat, muscle, bone, etc.), degree of pain, and the like. Time variables can be used in treatments that require, for example, maintenance of dose.

With continued reference to FIG. 2, the control assembly 130 includes a display 140 and a user input 142. The display 140 can be a monitor, screen, digital output, or the like. The display 140, in some embodiments, is used to monitor and evaluate the energy treatment. The control assembly 130 may also include, without limitation, a controller (or programmable circuitry) that commands the energy delivery device 110, for example, to selectively energize a set of energy emitters of the delivery device 110 so as to produce a field of light that matches the shape of the target site based, at least in part, on at least one parameter inputted using the user input 142.

The user input 142 can include, without limitation, one or more keyboards, touch pads, touch screens, dials, or switches, as well as other devices for programming the control assembly 130. If the control assembly 130 has stored programs, the user input 142 is used to select an appropriate treatment program.

The control assembly 130 also includes a power supply 150 (shown in phantom line in FIG. 2). The illustrated power supply 150 is a battery capable of delivering a sufficient amount of power to operate of the energy delivery device 110. As used herein, the term "power supply" includes, but is not limited to, one or more lithium batteries, chemical battery cells, super- or ultra-capacitors, fuel cells, secondary cells, thin film secondary cells, button cells, lithium ion cells, zinc air cells, nickel metal hydride cells, paper batteries (e.g., POWER PAPER®), printed power sources, and the like. The power supply 150 may be rechargeable or non-rechargeable. If the energy delivery device 110 or the entire energy treatment system 100 is disposable, the power supply 150 can be non-rechargeable. In some embodiments, the power supply 150 is hermetically sealed in a housing 152. Accordingly, the control assembly 130 lacks access to recharge the power supply 150 or induction recharge capability. If the energy delivery device 110 or the entire treatment system 100 is reusable, the power supply 150 can be rechargeable.

In some embodiments, including the illustrated embodiment of FIG. 2, the control assembly 130 includes a discharge module 151 adapted to selectively discharge the power supply 150. The discharge module 151 can therefore prevent reuse of the control assembly 130 after a certain number of treatments, even after a single treatment. In some embodiments, the discharge module 151 may also cause the system 100 to be permanently inoperable after a single use. Determining the duration of the single use may be accomplished by using a timer or an appropriate type of sensor such as a heat sensor, pressure sensor, light sensor, combinations thereof, or other sensors. In some embodiments, the module 151 includes one or more chemical fuses, which after receiving a deactivation signal, operate to destroy at least a portion of internal circuitry.

Figure 3:
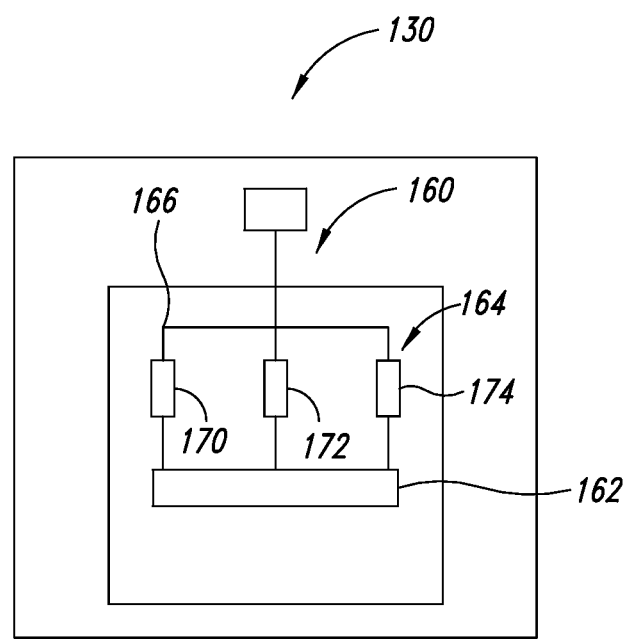
FIG. 3 is a schematic view of a controller of a control assembly, according to one illustrated embodiment.

FIG. 3 shows a controller 160 of the control assembly 130 having a control subsystem 162 in communication with one or more memory devices 164. One or more buses 166 link the power supply 150 to the control subsystem 162. The controller 160 provides one or more control signals over the bus 166 to operate the delivery device 110 and may also process signals received over the bus 166 from a photodiode or other sensor. The control subsystem 162 can take a variety of forms, including, for example, one or more microprocessors, Digital Signal Processors (DSPs), Field Programmable Gate Arrays (FPGA), and/or Application-Specific Integrated Circuits (ASICs).

The memories 164 may take a variety of forms, including, for example, one or more buffers 170, registers (not shown), random access memories (RAMs) 172, and/or read only memories (ROMs) 174. The buffer 170 may temporarily store data received from a feedback device (e.g., a sensor) until the control subsystem 162 is ready to process the data. The ROM 174 can persistently store instructions and/or data executable by the control subsystem 162. The RAM 172 may dynamically store instructions and/or data for use by the control subsystem 162. Other types of circuitry can also be employed.

The control assembly 130, in some embodiments, can have a closed loop or open loop system. For example, the control assembly 130 can have a closed loop system, whereby the power to the delivery device 110 is controlled based upon feedback signals from one or more sensors (e.g., the temperature sensors, photodiodes, and the like) configured to detect and transmit (or send) one or more signals indicative of temperature, pressure, light energy, or any other measurable parameters of interest. Based on those readings, the control assembly 130 can then adjust operation of the delivery device 110. Alternatively, the energy treatment system 100 can be an open loop system wherein the amount of stimulation produced by the energy delivery device 110 is set by user input. For example, the energy delivery device 110 may be set to a fixed power mode. It is contemplated that the energy treatment system 100 can be repeatedly switched between a closed and an open loop system.

Figure 4:
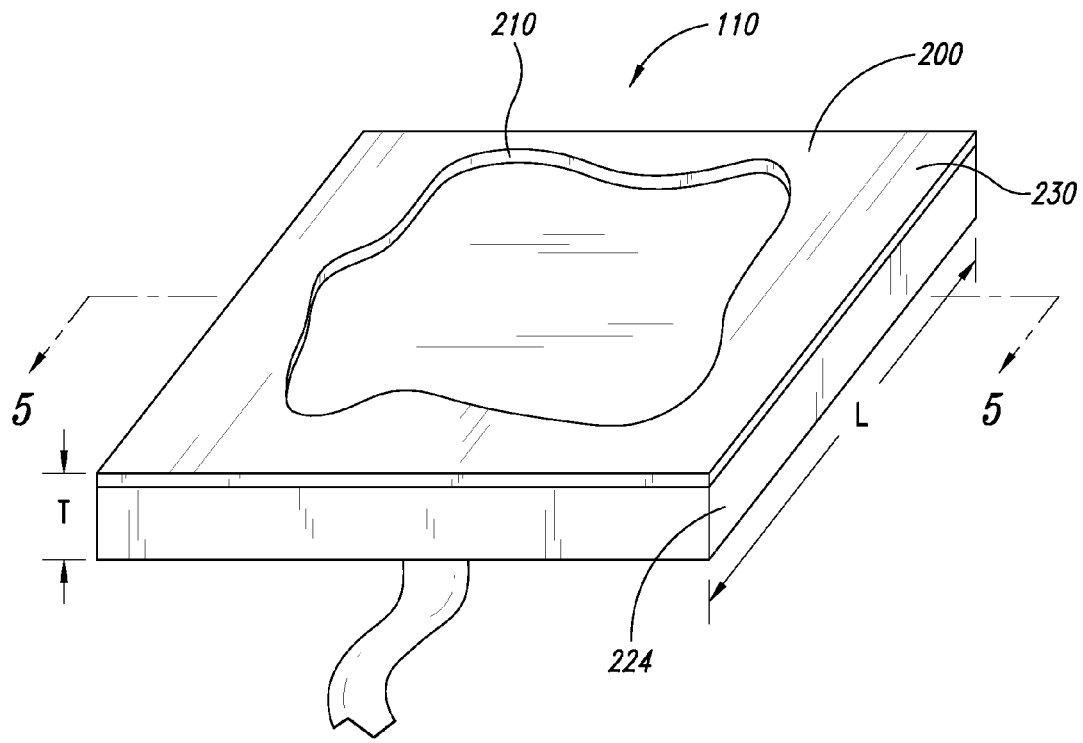
FIG. 4 is an isometric view of an energy delivery device having an optical window, according to one illustrated embodiment.
Figure 5:
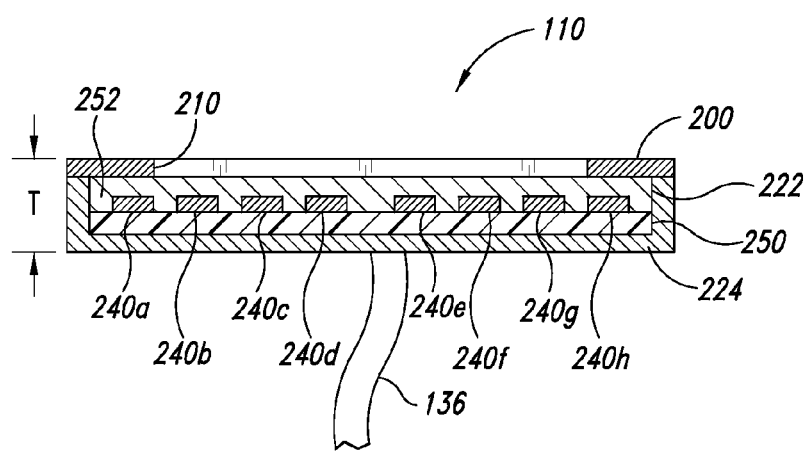
FIG. 5 is a cross-sectional view of the external energy delivery device of FIG. 4 taken along the line 5-5.

FIGS. 4 and 5 show the delivery device 110 including a mask 200, an optical window 210 defined by the mask 200, and an energy generating assembly 222. A protective housing 224 and the mask 200 cooperate to surround the energy generating assembly 222. The window 210 is positioned with respect to the energy generating assembly 222 such that energy from the assembly 222 passes through the window 210 and reaches the biological surface of the subject next to the window 210. For highly localized energy treatment, the window 210 may produce a field of light that approximately matches the desired target site so as to reduce, limit, or substantially eliminate unwanted energy delivery to tissue outside of the target site. As used herein, the term "optical window" generally refers to, without limitation, one or more apertures, openings, or transparent or translucent portions of a mask.

The mask 200 of FIG. 4 has an energy blocking portion 230 surrounding the window 210. The energy blocking portion 230 can block a sufficient amount of energy to prevent activation of the photoactive agent in the tissue directly beneath the blocking portion 230. The tissue beneath the blocking portion 230 is therefore not irreversibly damaged.

The illustrated mask 200 is in the form of a shield made, in whole or in part, of a non-transmissive material, such as an optically opaque material, reflective material, Mylar film, and the like. Additives (e.g., opacification agents, scattering agents, etc.), coatings (e.g., reflective coatings), diffusers, or combinations thereof can be utilized to render the mask 200 partially transmissive or non-transmissive. Opacification agents can include, but are not limited to, dyes, pigments, metal particulates, or metal powder, as well as other materials that can be coated onto, disbursed throughout, or otherwise integrated into the mask 200. If desired, the mask 200 can serve as a filter to absorb or reflect one or more wavelengths or wavebands.

In the illustrated embodiment of FIG. 5, the window 210 is an aperture positioned alongside the energy generating assembly 222. A substantial portion of the energy emitted by the energy generating assembly 222 passes through the window 210. In some embodiments, a majority of the light produced by the energy generating assembly 222 passes through the window 210. The window 210 can have any shape, including, but not limited to, a polygonal shape (e.g., rectangular shape, square shape, and the like), circular shape, elliptical shape, combinations thereof, irregular shapes, or other suitable shapes. In some embodiments, the window 210 and the target site can have complementary shapes.

The window 210 can be formed based on the treatment area. Tracings, stencils, captured images, and the like can be used to form the window 210. In some embodiments, for example, an image is taken of the desired treatment area. That image is then transferred onto a sheet. A portion of the sheet corresponding to the desired treatment area is removed, thereby forming the window 210 that matches the treatment area. In some embodiments, a sheet can be applied directly to the subject's skin. The treatment area can be manually traced onto the sheet, and the traced portion of the sheet can be removed to form the window 210. Other types of techniques can also be used.

In some embodiments, the window 210 can be formed, in whole or in part, of a transmissive material, such as an optically clear polymer or plastic. When the energy delivery device 110 is placed against the subject, the window 210 maintains separation of the energy generating assembly 222 and the subject's skin. The window 210 can prevent burning of the subject by the energy generating assembly 222.

With continued reference to FIG. 5, the energy generating assembly 222 includes a plurality of energy emitters 240*a-h* (collectively 240) mounted on a flexible substrate 250. The illustrated energy emitters 240 are embedded in an encapsulant 252 sandwiched between the window 210 and the flexible substrate 250. In some embodiments, the substrate 250 can function as a reflector such that internally reflected light is reflected by the substrate 250 towards the window 210.

An array of evenly or unevenly spaced energy emitters 240 can provide uniform or non-uniform energy fields, respectively. The illustrated array of evenly spaced light emitters 240 is capable of generating a substantially uniform energy field when activated. The energy field may define an area of illumination on the subject's skin. The area of illumination may have a size that is equal to or less than about 4 $cm^2$, 10 $cm^2$, 20 $cm^2$, 50 $cm^2$, or 100 $cm^2$. Other areas are also possible.

The energy emitters 240 may be disposed on conductive traces electrically connected to leads extending proximally through the connector 136 to the control assembly 130. Leads, connectors, and other types of circuitry can be incorporated into the energy generating assembly 222 to provide power to the energy emitters 240. U.S. Pat. No. 6,096,066 discloses various types of components (e.g., circuitry, microcontroller circuits, and agents or drugs) that can be integrated into or used with the energy treatment system 100. U.S. Pat. No. 6,096,066 is incorporated by reference in its entirety.

The energy emitters 240 in the form of light sources are capable of outputting visible light waves, non-visible light waves, and combinations thereof. Energy sources can be, without limitation, light emitting diodes (LEDs) (such as edge emitting LEDs, surface emitting LEDs, super luminescent LEDs, or organic LEDs), light-emitting polymers, laser diodes, lasers, electroluminescent devices, or other sources of energy capable of outputting energy suitable for performing energy treatments. For example, applicant's co-pending patent application U.S. Publication No. 2005/0228260 (U.S. patent application Ser. No. 10/799,357); U.S. Pat. No. 5,800,478; U.S. Pat. No. 6,096,066; and U.S. Pat. No. 7,018,395 disclose various types of energy emitters, elements, circuitry, and other components that can be utilized in the energy generating device 222. Each of these references is incorporated by reference in its entirety.

The illustrated energy emitters 240 of FIG. 5 can emit radiation wavelength(s) or waveband(s) that correspond with, or at least overlap with, the wavelength(s) or waveband(s) that excite or otherwise activate a photoreactive agent. Photoreactive agents can often have one or more absorption wavelengths or wavebands that excite them to produce substances that interact with the subject's tissue.

The delivery device 110 of FIGS. 4 and 5 has a relatively thin cross-sectional profile. In some embodiments, the delivery device 110 has a thickness t that is equal to or less than about 50%, 40%, 30%, 20%, or 10% of at least one of its transverse dimensions (e.g., a minimum transverse dimension, a maximum transverse dimension, or the like). For example, if the delivery device 110 has a generally rectangular shape as viewed from above (see FIG. 4), the thickness t of the delivery device 110 can be equal to or less than about 10% of a length L of the delivery device 110. In some embodiments, the delivery device 110 has an average thickness t that is equal to or less than about 50%, 40%, 30%, 20%, or 10% of its average transverse outer dimension.

FIGS. 6 to 9 illustrate one exemplary method of performing energy treatment on a subject. Generally, a photoreactive agent is delivered to a target site 260 of a subject 270 as discussed in greater detail below. The energy delivery device 110 is applied to the target site 260, and energy is transcutaneously delivered towards the target site 260 to excite the photoreactive agent. The photoreactive agent may kill, damage, induce tissue apoptosis in, or induce tissue necrosis in one or more anatomical features at the target site 260. Tissue outside of the targeted site 260, even tissue immediately adjacent the target site 260, may not be affected by the emitted light. Accordingly, the delivery device 110 provides highly localized energy treatment while reducing, limiting, or substantially limiting unwanted collateral treatment a non-targeted tissue.

Various types of photoreactive agents can be used. As used herein, the term "photoreactive agent" is broadly construed to include, without limitation, one or more drugs that can be activated with electromagnetic energy. A photoreactive agent can be a single photoreactive agent or a combination of photoreactive agents.

As noted above, in one particular embodiment, the photoreactive drug is talaporfin sodium. Talaporfin sodium is a chemically synthesized photosensitizer, having an absorption spectrum that exhibits a maximum peak at a desired wavelength, such as 664 nm. In one embodiment, the talaporfin sodium is presented as a lyophilized powder for reconstitution. One hundred milligrams of talaporfin sodium is reconstituted with 4 milliliters of 0.9% isotonic sterile sodium chloride solution, to give a solution at a concentration of 25 mg/ml.

A dose of talaporfin sodium is administered intravenously to the patient at 1 mg/kg, over a period of 3 to 5 minutes. After, during, and/or before administration of the selected photoactive agent in an appropriate dose, the external device 110 is positioned on a patient at a preselected location appropriate to treat the targeted tissue.

In one embodiment, the drug is activated with energy within the electromagnetic spectrum, the energy being measured in Joules (J) per centimeter of length of the energy generating assembly 222. Likewise, the energy fluence is measured in milli-watts (mW) per centimeter of length of the energy generating assembly 222. The amount of energy delivered may depend on one or more factors, such as the photoreactive agent used, the dose administered, the type of tissue being treated, and/or the proximity of the light array 240 to the tissue being treated. The energy (E) delivered is the product of the fluence (F) and the time period (T) over which the fluence is delivered: $E=F\times T$. The fluence may be delivered for only a fraction of the treatment time, because the energy generating assembly 222 may be pulsed, for example in a frequency such as 60 kHz, or may be controlled by a timing pattern. An example of a timing pattern is that the array 240 is at full fluence for 20 seconds, then off for 10 seconds in a repetitive cycle. Of course, any pattern and cycle that is expected to be useful in a particular procedure may be used.

In accordance with an embodiment, fifteen minutes to one hour following talaporfin sodium administration, light energy in the range from about 50 to about 1000 J/cm with a light fluence in the range from about 5 to about 50 mW/cm is delivered to the treatment site. As may be expected, the equation discussed above relating energy, time, and fluence plays a role in selection of the fluence and energy delivered. For example, depending upon the patient, a certain time period may be selected as suitable. In addition, the nature of treatment might dictate the energy required. Thus, fluence F is then determined by $F=E/T$. The energy generating assembly 222 should be capable of providing that fluence in the allotted time period. For example, if a total of 200 J/cm of light energy may be delivered to the treatment site at 20 mW/cm of light fluence, then the treatment period is less than 3 hours. In some embodiments, the total of 200 J/cm of light energy may be delivered to the treatment site at 20 mW/cm of light fluence for a treatment period that is less than 1 hour.

Infrared light, visible light, and/or ultraviolet light can be emitted by the energy generating assembly 222. In some embodiments, the light emitters 240 emit light with a peak wavelength at 660 nm±5 nm. More than 80% of the power output is within ±20 nm of the peak wavelength, namely the light catheter emits light at a wavelength of about 640-680 nm. The spectral bandwidth of the energy emitters provides a significant overlap with the talaporfin sodium absorption curve in the 660 nm region.

Figure 6:
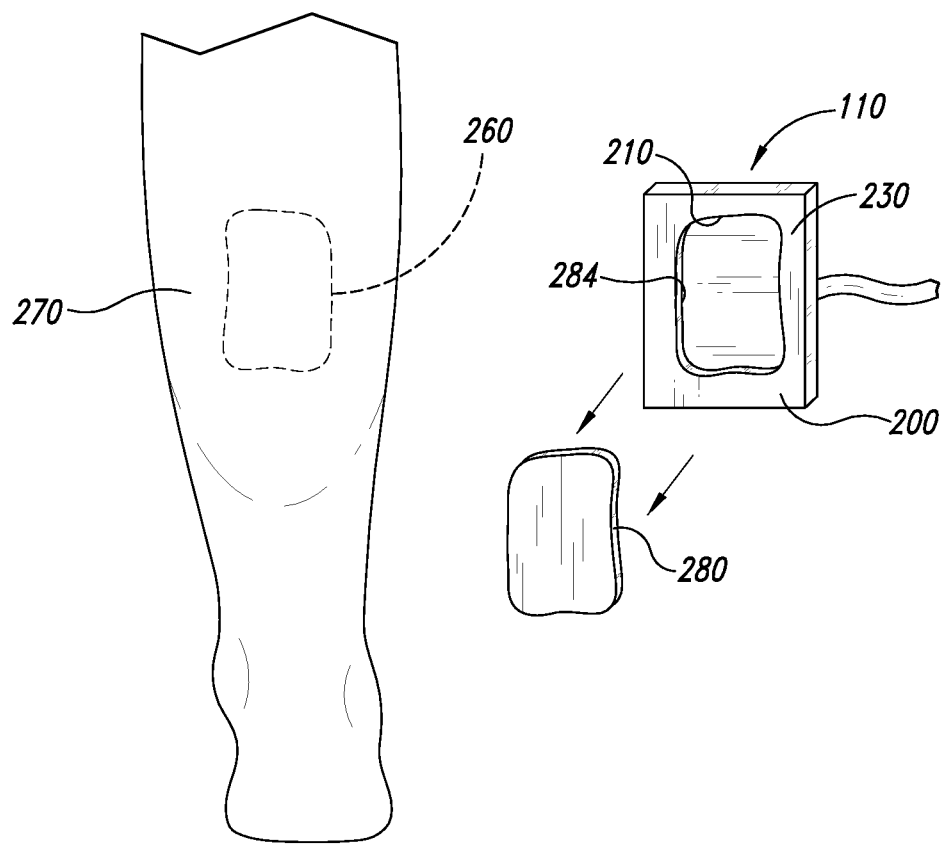
FIG. 6 shows a targeted site of a subject and an external energy delivery device ready to be positioned over the targeted site, according to one illustrated embodiment.

With continued reference to FIG. 6, the illustrated target site 260 can be identified using various techniques. The target site 260 may include various types of unwanted tissue, such as aesthetically unattractive anatomical structures, visible blood vessels, spider veins, skin abnormalities, discolorations, cancerous cells, skin markings (e.g., tattoos), and other unwanted features. Invasive methods of identifying an appropriate target site may employ catheters, imaging tools, internal scanners, and the like. These types of instruments may be percutaneously delivered into the subject to provide in situ imaging of vessel walls or other attributes useful in developing a treatment program.

Non-invasive visual inspection is a convenient and inexpensive way to evaluate the target site. For example, spider veins may be red, blue, or purple and, consequently, are readily distinguishable from other tissue. Accordingly, a subject with spider veins can be visually inspected with the naked eye or with a non-invasive instrument.

In one example embodiment, the illustrated target site 260 includes a visually recognizable network of spider veins. In some procedures, the network of spider veins may be visible by the naked eye from a distance of at least 1 meter but may be visibility unrecognizable after performing one or more light treatments from a distance of at least 1 meter. In some procedures, for example, the pretreatment network of spider veins may be visible by the naked eye from a distance of at least 5 meters but may be visibly unrecognizable, after performing one or more light treatments, from a distance of at least 3 meters. The reduction in visibility can be selected based on the desired cosmetic appearance.

To form the treatment window 210 that generally matches the shape of the target site 260, a section 280 of the mask 200 is removed from the delivery device 110, thereby forming the energy blocking portion 230 and the window 210. Of course, the target site 260 may include some healthy untargeted tissues interposed between the targeted vessels. Depending on the light treatment, the untargeted tissue may or may not be affected by the emitted energy.

Figure 7:
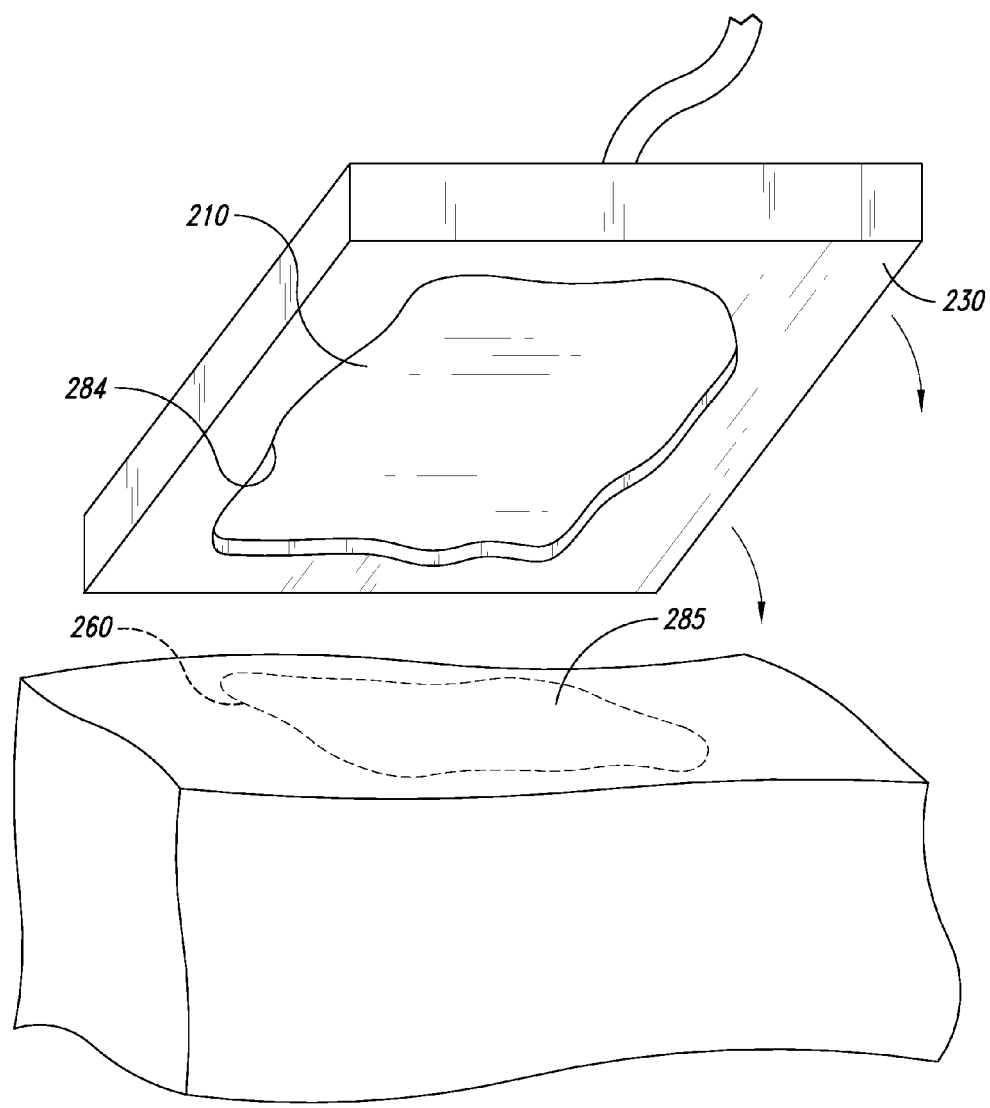
FIG. 7 shows an external energy delivery device being applied to a targeted site, according to one illustrated embodiment.

Referring to FIGS. 6 and 7, an inner edge or boundary 284 of the energy blocking portion 230 can be aligned with and proximate to a periphery 285 of the target site 260. The inner edge 284 is then mated with the periphery 285 of the target site 260. If the inner edge 284 closely matches the boundaries of the spider veins, the entire spider vein may be treated in a single treatment. In various embodiments, the inner edge 284 can be positioned slightly inside or outside of an outer boundary of the network of spider veins. The mask 200 can substantially prevent light from reaching tissue outside the outer boundary of the target site 260 (e.g., tissue located laterally away from the mask 200).

Figure 8:
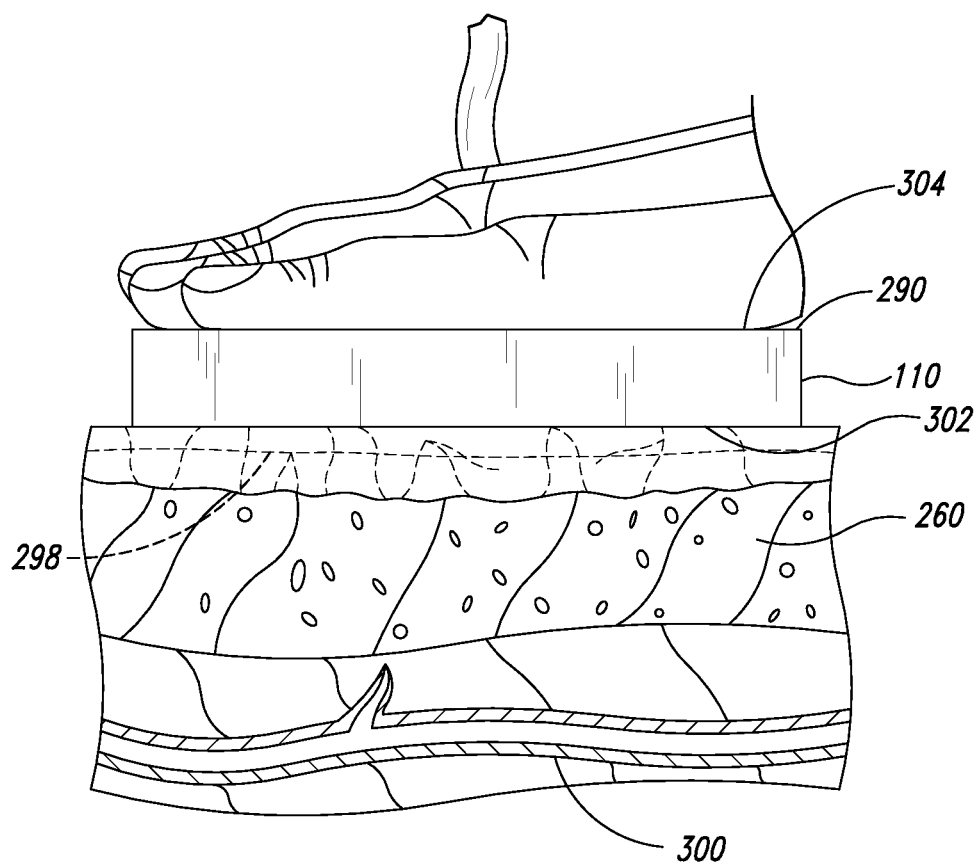
FIG. 8 shows the external energy delivery device held against the targeted site, according to one illustrated embodiment.

In one embodiment, as shown in FIG. 8, once the delivery device 110 is placed against the subject, pressure can be manually applied to a back surface 290 of the delivery device 110 if desired to enhance energy delivery to the targeted the blood vessels 298 (illustrated as spider veins in phantom line). Additionally or alternatively, the illustrated delivery device 110 can also treat deeper varicose veins 300 (shown in phantom).

The illustrated delivery device 110 of FIG. 8 has a pair of opposing longitudinal sides 302, 304 and is adapted to output most of the energy outputted by the energy emitters from the longitudinal side 302 facing the subject. The emitted energy passes through tissue between the delivery device 110 and the targeted spider veins 298 and ultimately reaches and activates a photoreactive agent in the spider veins 298. The entire network of spider veins 298 can be thoroughly illuminated while keeping the energy delivery device 110 stationary with respect to the targeted spider veins 298.

In the context of the treatment of blood vessels, the photoreactive agent may be distributed to the internal vessel wall before the vessel is illuminated. As noted above, the wavelength of waveband can substantially correspond to the absorption wavelength or waveband or the photoreactive agent in the spider veins 298 to cause the agent to undergo a photochemical reaction that causes a desired response. The photoreactive agent may undergo a reaction to cause localized damage, apoptosis, cell lysis or necrosis, thereby resulting in ablation, destruction, and/or closure of the spider veins 298. The spider veins 298 can then be reabsorbed by surrounding tissue. Healthy vessels around the closed spider veins 298 can restore the normal flow of blood and often may alleviate or eliminate symptoms, if any. Surrounding blood vessels connected to the treated spider veins 298 may also shrink after the treatment. Of course, blood vessels connected to the treated spider veins 298 can likewise be treated, if needed or desired.

The total light dose provided by the delivery device 110 can be less than about 1000 J, 500 J, 100 J, or ranges encompassing such total light doses. For example, the total light dose can be between about 5 J and about 40 J. Such doses are particularly well suited for significantly reducing the visibility of relatively small blood vessels (e.g., spider veins) or other shallow targeted features. For some treatments of spider veins, the maximum distance at which the network of spider veins is visually identifiable with the naked eye with approximately 20/20 vision is reduced at least about 2 meters, 1 meter, or 0.5 meter. The light irradiance can be less than about 100 mW/cm$^2$. Such light irradiance is particularly well suited to significantly reduce the visibility of spider veins, or other types of visible blood vessels. In some embodiments, the light irradiance is between about 10 mW/cm$^2$ and about 40 mW/cm$^2$. The light can be administered by the energy delivery device 110 within about 5 minutes after administering the photoreactive agent to the target blood vessels. In some embodiments, the light is administered by the energy delivery device 110 within about 3 minutes after administering the photoreactive agent. For example, the light could be administered immediately after injecting photoreactive agent into spider veins. Other light doses, light irradiances, and lengths of treatment are also possible to diminish the visibility of the network of blood vessels without altering an appearance of the subject's skin (e.g., color tone, optical properties, and the like) at the target site.

The photoreactive agent can be administered to the patient before, during, or after the delivery device 110 is positioned on the subject's body. The photoreactive agent can be administered systemically or locally, or both. Systemic administration can be via an injection, such as an intravenous injection. Local administration can include, without limitation, topical delivery using a photoreactive gel or a photoreactive cream that is applied directly to the subject at or near the target site or by direct injection into the target vessels with or without viewing aid. In some embodiments, the photoreactive agent is carried by the delivery device 110 and then delivered by liposomal, transdermal, and/or iontophoretic techniques. For example, the mask 200 can be coated, impregnated, or otherwise treated with photoreactive agent for delivery upon contact with the subject. The delivery technique can be selected based on the desired length of treatment, depth of targeted tissue, and other parameters known in the art.

In some cosmetic treatments, the energy treatment system 100 can treat shallow blood vessels, spider veins, skin abnormalities, skin discolorations, skin markings (e.g., tattoos), and other unwanted features which may significantly impact the appearance of the subject. Even though these may cause only cosmetic problems, the energy treatment system 100 may be used to reduce or substantially eliminate the appearance of these types of imperfections to achieve, for example, a naturally appearing skin with normal skin color and a smooth contour. Any number of treatment procedures may be performed to achieve the desired overall appearance.

Pressure can be applied to the treatment area to at least partially close the passageways of the treated vessels by, for example, compressing the vessel walls. The blood vessel can be mechanically collapsed or compressed by applying pressure, via vacuuming, and/or by any other suitable method to maintain a collapsed state for a time sufficient to allow the opposing walls of the blood vessel to weld together.

Figure 9:
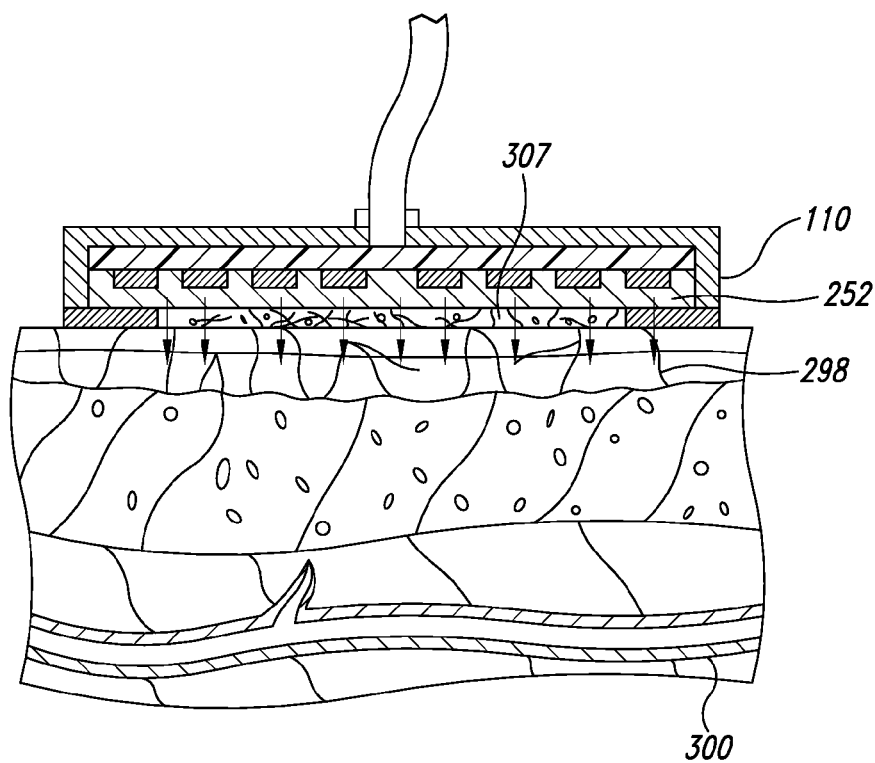
FIG. 9 is a cross-sectional view of the external energy delivery device and the targeted site of FIG. 8, according to one illustrated embodiment.

Various types of energy conductive mediums can be used to control the delivery of energy. FIG. 9 shows a light conductive medium 307 between the delivery device 110 and the subject. The light conductive medium 307 is an optical coupler that facilitates delivery of light to the subject by increasing or decreasing internal reflectance, adjusting the path of travel of the light rays, adjusting the bending of light, and the like. For example, the encapsulant 252 may have a first index of refraction $\eta 1$ and the medium 307 may have a second index of refraction $\eta 2$ selected to increase or decrease internal reflectance and/or bending of light. It is understood that the "index of refraction," as used herein, is the factor by which the phase velocity of electromagnetic radiation is slowed relative to a vacuum and is usually identified by the Latin symbol $\eta$.

In some embodiments, the index of reflection $\eta 1$ can be approximately equal, or equal, to the second index of refraction $\eta 2$. For example, the first and second indexes of refraction $\eta 1$, $\eta 2$ can be in the range of 1.33-2.0. In some embodiments, the encapsulant 252 is made, in whole or in part, of a substantially transparent material (e.g., an optical epoxy or another type of flexible polymer or thermoplastic material) that allows for the transmission of light therethrough. The medium 307 can be made of a translucent gel with similar optical characteristics.

The second index of refraction $\eta 2$ may be selected to be approximately equal to, or equal to, an index of refraction of the subject's tissue at the target site. It is appreciated that in practice it is difficult to match or substantially match the second index of refraction $\eta 2$ of the medium 307 to the index of refraction of the subject's dermis, thus the objective may be to at least match the second index of refraction $\eta 2$ to be as practically close as possible to the index of refraction of the dermis. In some embodiments, the second index of refraction of $\eta 2$ is 1.33-1.5. In some embodiments, the second index of refraction $\eta 2$ of the medium 307 is selected to be lower than, equal to, or greater than the first index of refraction $\eta 1$ of the encapsulant 252 and/or the index of refraction of the subject's tissue.

Thus, in some embodiments, light is transmitted to the target site by transitioning the light through selective indices of refraction, such as from the first index of refraction $\eta 1$ of the encapsulant 252 to a second index of refraction $\eta 2$ of the medium 307. By providing the delivery device 110 with a refractive index gradient, light may be advantageously directed more accurately and/or more efficiently toward the targeted site.

In some embodiments, the delivery device 110 is operable to generate a maximum illumination field of light. The control assembly 130 is operable to energize only a portion of the plurality of light emitters 240 so as to produce a treatment illumination field of light that is smaller than the maximum illumination field of light and that substantially matches a shape of a target site based, at least in part, on at least one parameter inputted into the control assembly 130. In such embodiments, the delivery device 110 without the mask 200 can generate the maximum illumination field of light. The optical window 230 defines the treatment illumination field of light that is smaller than the maximum field of light, even when all the light emitters 240 are activated.

The light emitters 240 may be separately controlled. For example, a first group of the light emitters 240 may be independently energized from another group of the light emitters 240. Electrical currents can be independently supplied to each different group of light emitters 240 to control the illumination field and/or light intensity produced by the light emitters in each group. Thus, for example, a group of the light emitters 240 can be energized longer or with a greater current, compared to that supplied to another group of the light emitters 240, to increase the intensity and/or the duration of the light produced by the corresponding groups of light emitters 240. By increasing the light output of certain light emitters 240, a more effective treatment of a deeper tissue can be achieved. Different groups of light emitters 240 can be configured and separately controlled based on the dimensions and shape of the target site. Of course, the pattern, spacing, and number of light emitters 240 can be selected to achieve a desired light. Additionally, the configuration of a particular group of light emitters 240 can be made to substantially match the configuration of the target sites. For example, the shape of the group of light emitters 240 can generally match the shape of a target site.

Figure 10:
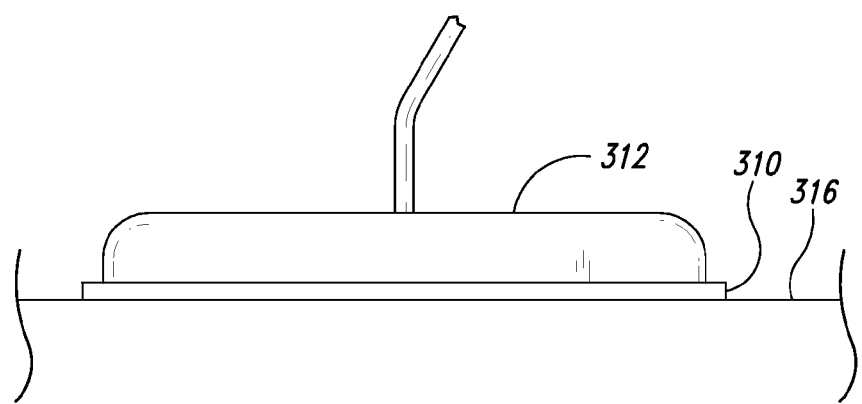
FIG. 10 is a side elevational view of an element positioned between an external energy delivery device and a subject, according to one illustrated embodiment.

Referring to FIG. 10, an element 310 is interposed in one embodiment between an energy delivery device 312 and a subject 316. The element 310 can be in the form of a diffuser capable of affecting the distribution of outputted energy to promote a desired energy field, for example a substantially uniform energy field. In some embodiments, the illustrated element 310 is a flexible conformable one-piece sheet that scatters light passing therethrough. In other embodiments, the element 310 is formed of a spreadable material, such as a gel or cream, having light scattering properties. Various types of light scattering additives can be incorporated into the spreadable material to obtain the desired optical characteristics.

The element 310 can also be an adhesive layer. In some embodiments, the element 310 is a double-sided adhesive sheet. The index of refraction of the element 310 can be selected to optimize the amount of energy delivered to the subject. In other embodiments, the element 310 is a single layer of an adhesive material. Example adhesive materials include, without limitation, adhesive gels, binding agents, and/or pressure sensitive adhesives. For example, the index of refraction of the element 310 can generally match the index of refraction of the subject's dermis so as to ensure efficient transcutaneous transmission.

In some embodiments, the element 310 can minimize, limit, or prevent unwanted trauma to the subject 316. If the energy delivery device 312 generates appreciable amounts of thermal energy, the element 310 can keep the dermis of the subject 316 at or below a desired temperature to prevent, for example, burning of the dermis. The element 310 can have one or more cooling channels for circulating a chilled fluid (e.g., chilled water), one or more peltier devices, or other types of cooling elements. In some embodiments, the element 310 can be transparent pouch that is applied to the subject 316 before energy delivery. The pouch can contain a chilled or frozen substance to cool the subject 316.

Figure 11:
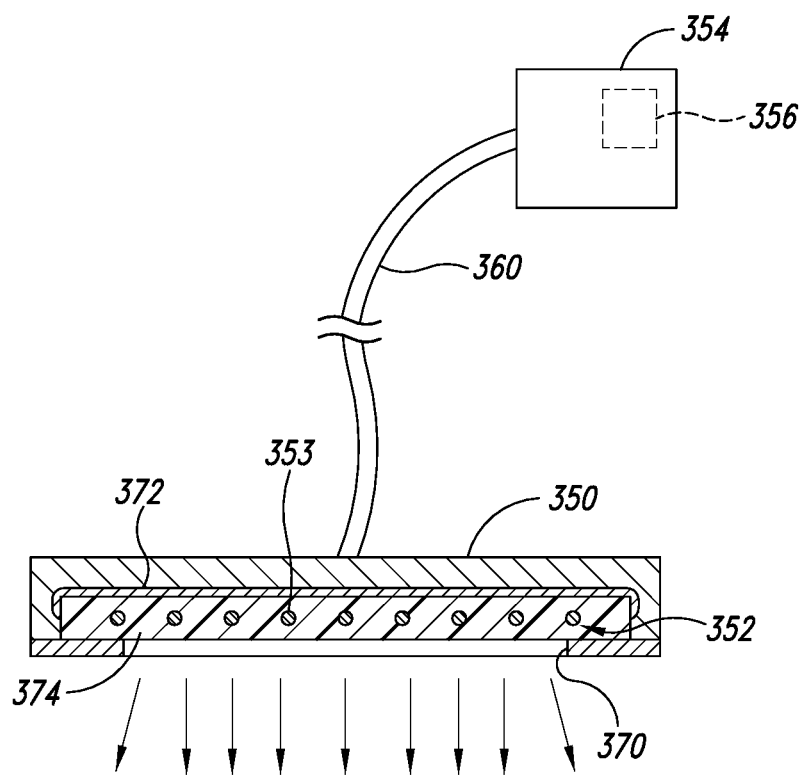
FIG. 11 is a partial cross-sectional view of an energy treatment system having a patch with a plurality of waveguides for emitting energy, according to one illustrated embodiment.

FIG. 11 shows an energy delivery device 350 that includes a panel 352 for outputting light. The panel 352 includes a plurality of spaced apart energy emitters 353. A control assembly 354 includes an energy source 356 (shown in phantom) that outputs energy delivered to the panel 352 via a connector 360. The energy is subsequently delivered out of the panel 352.

The energy emitters 353 of FIG. 11 are longitudinally-extending waveguides suitable for transmitting electromagnetic waves outputted by the power supply 356 in the form of a light source. The waveguides can be optical fibers, transmission conduits, optical waveguides, or other types of electromagnetic waveguides. For example, each energy emitter 353 can be a single optical fiber or a plurality of optical fibers (e.g., a bundle of optical fibers).

Diffusers, reflectors, and other components can help direct energy through an optical window 370 laterally spaced from the energy fibers 253. In some embodiments, including the illustrated embodiment of FIG. 11, a reflector 372 opposing the optical window 370 can reflect light outputted from the panel 352 towards the optical window 370, thereby increasing the amount of energy that reaches the target site. An encapsulant 374 interposed between the reflector 372 and the window 370 can be made, in whole or in part, of a flexible material such that the energy delivery device 350 conforms closely to the skin of the subject.

The energy source 356 can include, but is not limited to, one or more light sources. Exemplary light sources include, without limitation, one or more LEDs, lasers (e.g., a gas laser such as an argon-ion laser, solid state laser, or other type of laser suitable for activating the photoreactive agent), and the like. The energy source 356 can be powered by an internal power supply or an external power supply (e.g., an AC outlet).

Figure 12:
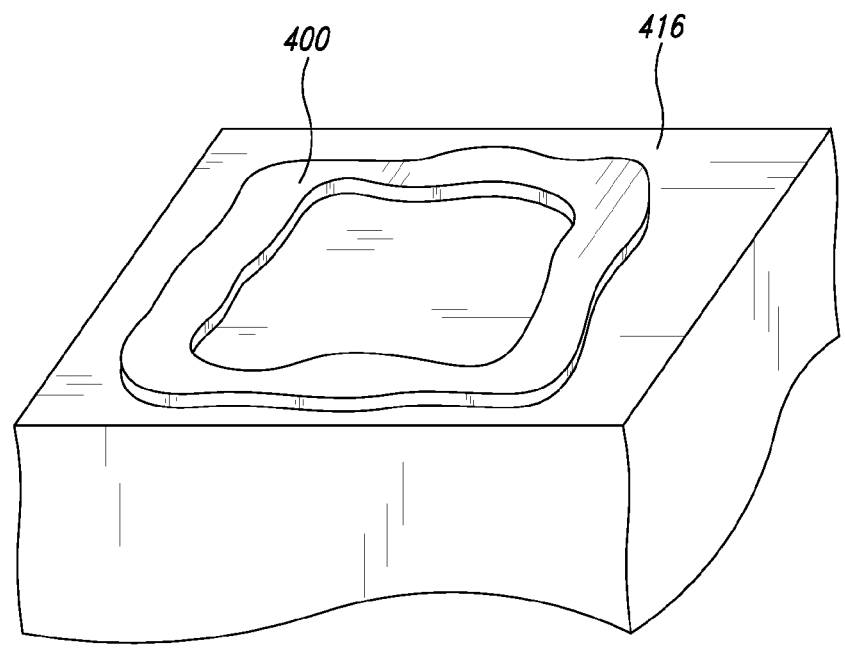
FIG. 12 is an isometric view of a mask applied to a subject, according to one illustrated embodiment.
Figure 13:
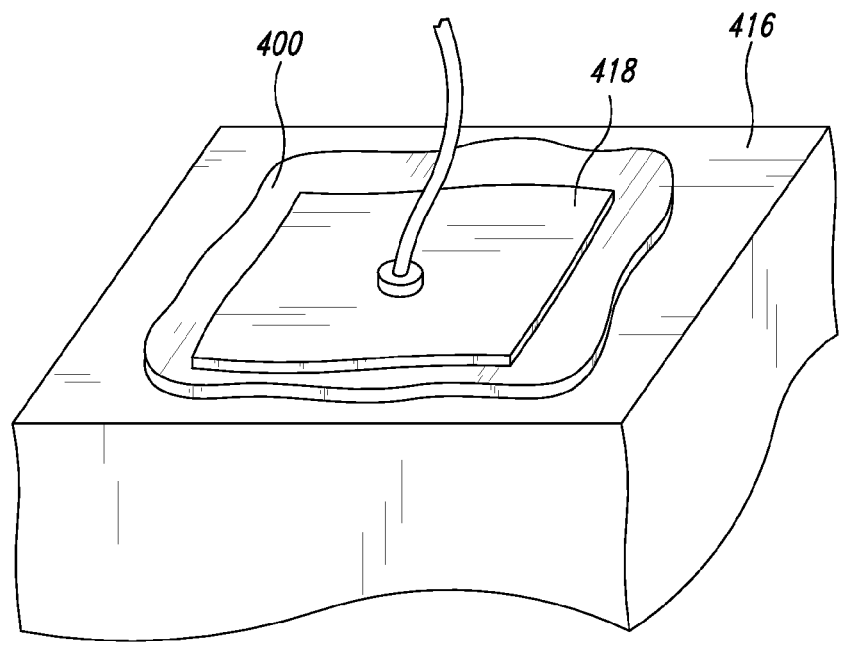
FIG. 13 is an isometric view of an external energy delivery device positioned upon the mask of FIG. 12.

FIGS. 12-13 show one method of using a mask 400 that is separate from an energy delivery device 418. The mask 400 can be applied to a subject and then inspected (e.g., visually inspected) to ensure proper alignment with the target site.

The mask 400 may be patterned based on one or more captured images of the targeted site or other types of targeting techniques. The mask 400 may be a patterned sheet that can be repositioned any number of times to assure proper alignment.

In some embodiments, the mask 400 is made of a spreadable material applied to a subject's skin 416. If the delivery device 418 of FIG. 13 emits light, the mask 400 can be formed, in whole or in part, of an opaque or semi-opaque spreadable material. Example spreadable materials include, but are not limited to, creams, gels, and other flowable materials with desired optical characteristics, including, without limitation, spreadability, viscosity, optical transmissivity, and the like. Additionally, the spreadable material may also include one or more additives including, without limitation, medicaments (e.g., photoreactive agents, antibiotics, anesthetics, and the like), colorants, dyes, and the like. For example, the spreadable material may include an anesthetic to help keep discomfort associated with the treatment at or below an acceptable level.

Figure 14:
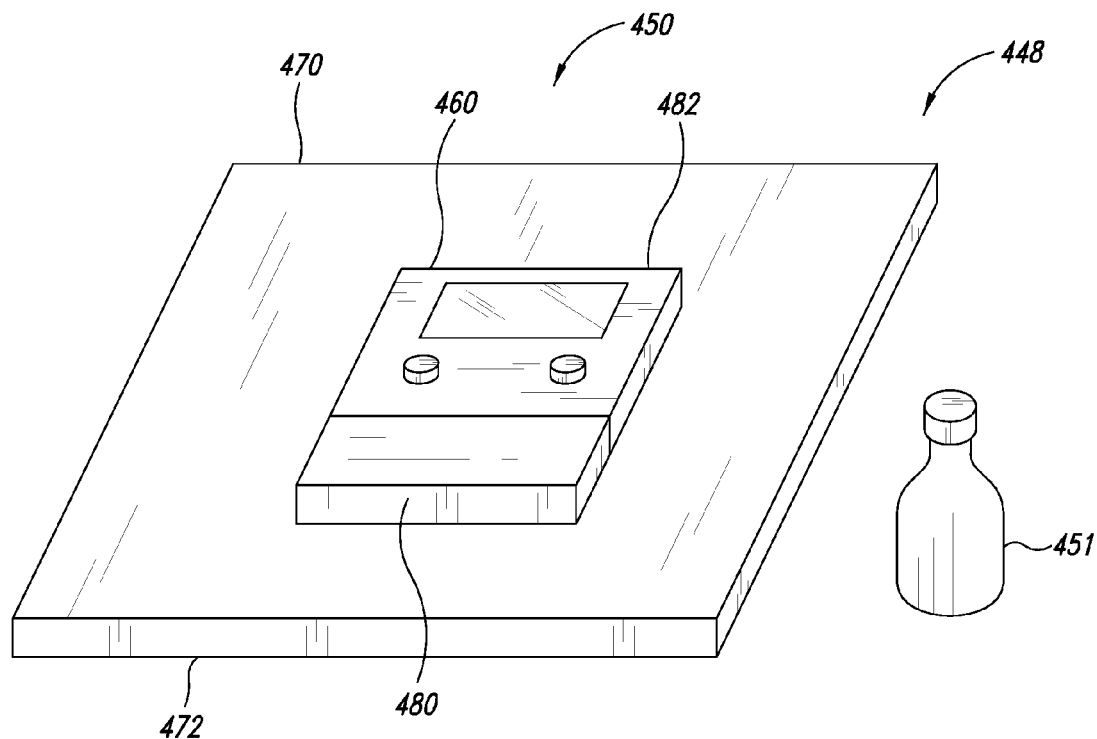
FIG. 14 is an isometric view of an energy treatment system including a modular external energy delivery device and a container of a drug, according to one illustrated embodiment.

FIG. 14 shows an energy treatment system 448 including an external delivery device 450 and a container 451 of a drug (e.g., photoreactive agent). The external delivery device 450 includes a control assembly 460 mounted on a patch 470. When a lower surface 472 of the patch 470 is placed against a subject, the control assembly 460 is readily accessible so that a user can conveniently control operation of the patch 470, even while the patch 470 is energized during treatment.

In some embodiments, including the illustrated embodiment, the energy treatment system 448 is disposable and has an integrated power supply 480 permanently coupled to or within a housing 482 of the control assembly 460. In some embodiments, the power supply 480 is a single-use power supply (e.g., a single-use battery) capable of outputting a sufficient amount of power to generate emitted energy via one or more energy emitters of the patch 470 for a single treatment program.

The energy treatment systems described herein can be packaged to keep them sterile. For example, one or more energy delivery devices, patches, control assemblies, masks, instructions for use, and/or connectors may be enclosed within packaging. A physician can open the sterile packaging immediately before performing a procedure. The kit may additionally or alternatively also include one or more medicaments.

Figure 15:
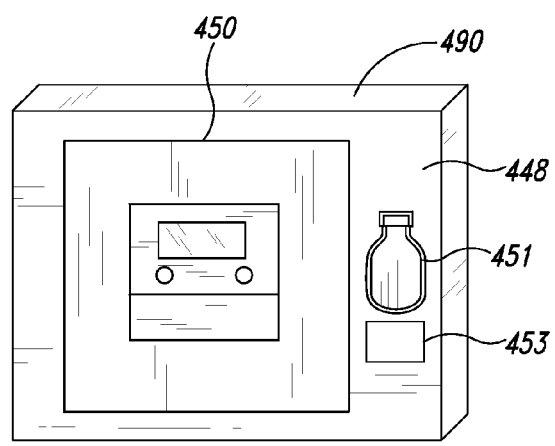
FIG. 15 illustrates a kit including a modular patch, a container of a drug, and instructions for use, according to one illustrated embodiment.

FIG. 15 shows a kit including an energy treatment system 448 within packaging 490. As used herein, the term "packaging" generally refers to, but is not limited to, rigid and flexible medical packaging. Example packaging includes, without limitation, sterile bags, medical pouches, trays, and the like. A physician can remove the delivery device 450, the container 451, and/or instructions-for-use 453 in order to perform a procedure.

Figure 16:
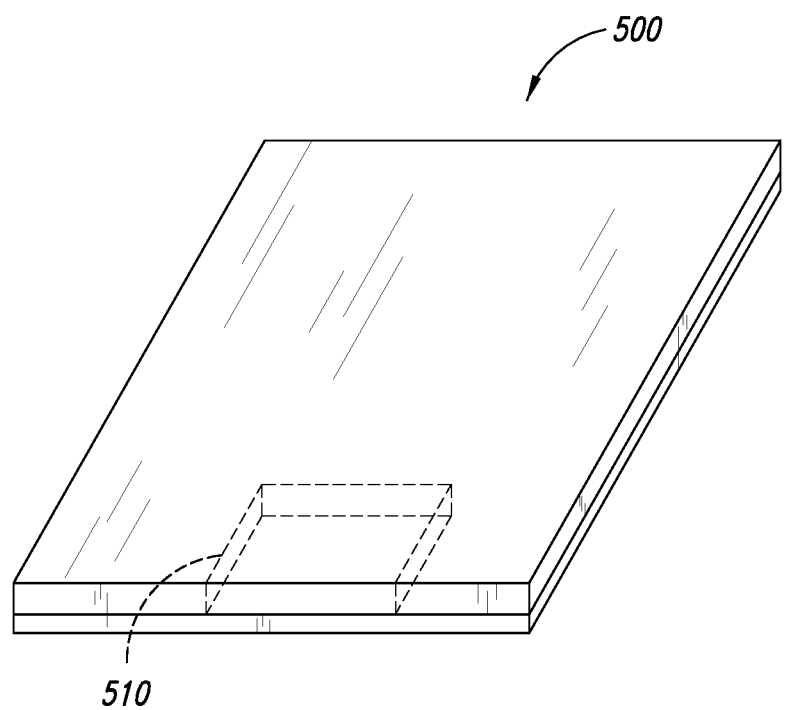
FIG. 16 is an isometric view of a patch having an internal power supply, according to one illustrated embodiment.

The patches disclosed herein may include one or more power supplies. FIG. 16 illustrates a patch 500 having an embedded internal power supply 510. If the patch 500 is applied to biological surfaces with complex geometries, the power supply 510 can be a flexible battery, such as a thin, flexible polymer battery (e.g., organic polymer batteries). Various types of control assemblies can be coupled to or integrated into the patch 500.

Figure 17:
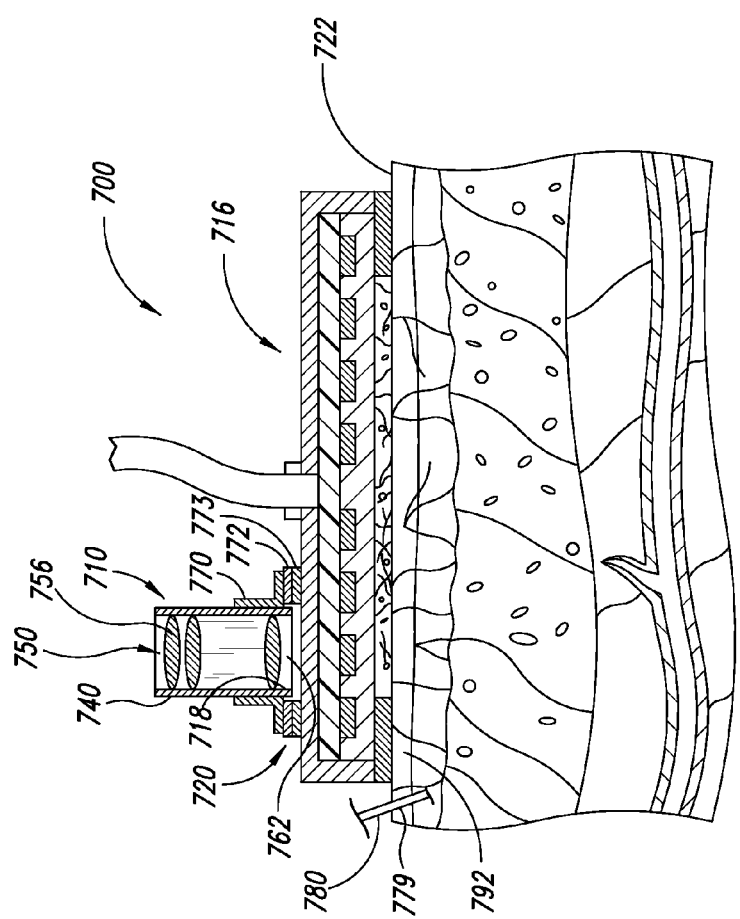
FIG. 17 is a side cross-sectional view of an energy treatment system that includes a visualization device, according to one illustrated embodiment.

FIG. 17 shows an energy treatment system 700 that includes a visualization device 710 for viewing the target site. The visualization device 710, in some embodiments, can be in the form of a magnifier that provides a desired level of optical magnification. The visualization device 710 can be coupled to a patch 716 or simply provided for use with the patch 716. For example, a kit, such as the kit illustrated in FIG. 15, can include a visualization device.

If coupled to the patch 716, as illustrated in FIG. 17, user can separate the visualization device 710 from the patch 716 and place a lower end 718 of the visualization device 710 against the subject's skin 722. The user can look through the visualization device 710 to view a magnified image of the target site in order to locate and/or evaluate features, such as small spider veins, having relatively small dimensions. The visualization device 710 could be used to aid in injection of the photosensitizer.

The visualization device 710 includes a main body 740 and an optical train 750 in the main body 740. The optical train 750 includes, in some embodiments, one or more lenses such as, for example, biconvex lenses, plano-concave lenses, converging lenses, diverging lenses, compound lenses, and the like. The illustrated optical train 750 includes eyepiece lenses 756 and an objective lens 762. Other types of optical trains can also be used to provide the desired amount of magnification, such as, for example, at least about 2× magnification, about 10× magnification, or about 20× magnification, or ranges encompassing such magnifications. Other amounts of magnification are also possible, if needed or desired.

A mounting feature 770 of the visualization device 710 can be coupled to a retaining assembly 720, which is fixedly coupled to the patch 716. For example, the mounting feature 770 can be magnetically coupled to or adhered to the retaining assembly 720. The illustrated mounting feature 770 includes one or more magnetic couplers 772 that magnetically couple to the magnetic couplers 773 of the retaining assembly. As used here, the term "magnetic coupler" can include, without limitation, one or more electromagnets, permanent magnets, elements made in whole or in part of ferromagnetic materials, or combinations thereof.

Figure 18:
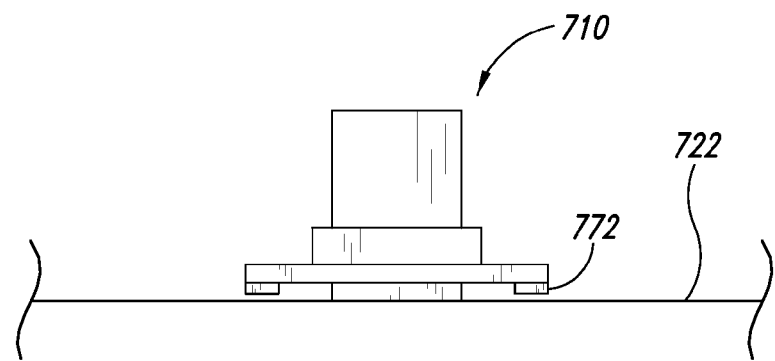
FIG. 18 is a side elevational view of a visualization device placed against a patient's skin.

FIG. 18 shows the visualization device 710 positioned on the subject's skin. A user can view the image provided by the device 710 to determine an appropriate access location 779, or injection site, as illustrated in FIG. 17. As discussed above, the photoreactive agent can be administered to the target site via local injection. For example, if spider veins are targeted, the user can locate the injection site 779 for delivering a photoreactive agent directly to the spider veins. As shown in FIG. 17, a delivery device 780, such as a needle, can be delivered at the injection site 779 and moved into the targeted site 792, illustrated as a spider vein. After performing the energy treatment, the visualization device 710 can be used to view and evaluate the effectiveness of the treatment.

Figure 19:
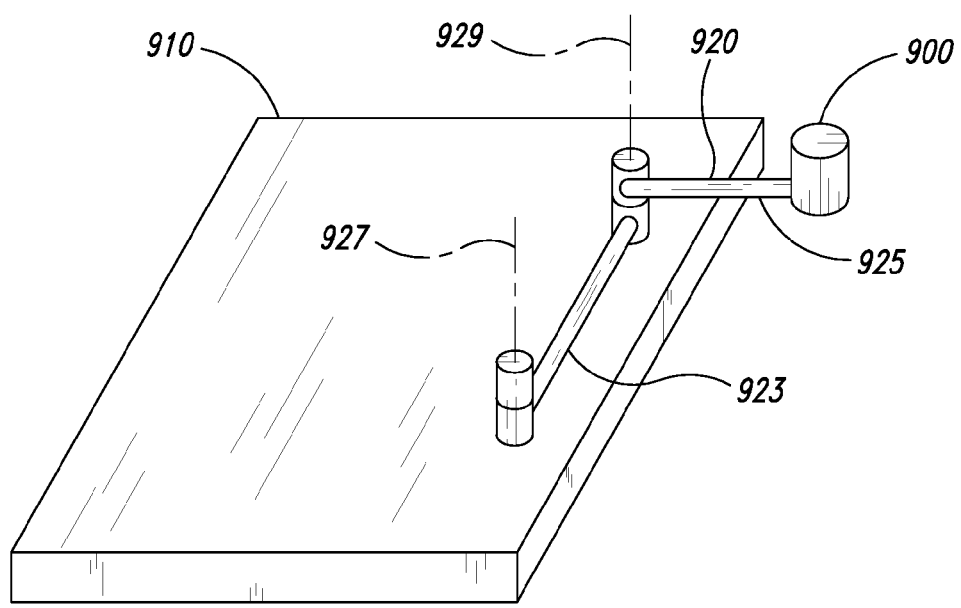
FIG. 19 is an isometric view of an energy treatment system that includes a visualization device movably coupled to a patch, according to one illustrated embodiment.

FIG. 19 shows a visualization device 900 mechanically connected to a patch 910 via a positioning assembly 920. The positioning assembly 920 can be operated to move the visualization device 900 from a stored position (e.g., a position above the patch 910) to a deployed viewing position (illustrated in FIG. 19). After viewing the subject, the visualization device 900 can be returned to the stored position for convenient transport.

The illustrated positioning assembly 920 includes a first arm 923 pivotally coupled to the patch 910 and a second arm 925 pivotally coupled to the first arm 923. The second arm 925 extends between the first arm 923 and the visualization device 900 and can be fixedly coupled to the visualization device 900. The first and second arms 923, 925 can pivot about first and second axes of rotation 927, 929.

Example positioning assemblies can also include one or more arms, linkage systems, rotators, joints, and the like. The type and configuration of the positioning assembly can be selected based on the size of the patch, treatment to be performed, configuration of the visualization device 900, and the like. Additionally, one or more visualization devices can be incorporated into the energy treatment systems described in connection with FIGS. 1, 2, 4, 5, and 6, for example, and a single energy treatment system can include any suitable number of visualization devices for providing flexibility in viewing the target site.

The above description of illustrated embodiments, including what is described in the Abstract, is not intended to be exhaustive or to limit the invention to the precise forms disclosed. Although specific embodiments and examples are described herein for illustrative purposes, various equivalent modifications can be made without departing from the spirit and scope of the invention, as will be recognized by those skilled in the relevant art.

All of the U.S. patents, U.S. patent application publications, U.S. patent applications, foreign patents, foreign patent applications and non-patent publications referred to in this specification and/or listed in the Application Data Sheet, to include U.S. Pat. Nos. 6,958,498; 6,784,460; 6,661,167; 6,445,011; and 6,096,066; U.S. Provisional Patent Application No. 60/879,508; U.S. Provisional Patent Application No. 60/879,466; U.S. Publication No. 2005/0228260; International Patent Application Nos. PCT/US2005/032851 and PCT/US2001/044046 are incorporated herein by reference, in their entirety. Except as described herein, the embodiments, features, systems, devices, materials, methods and techniques described herein may, in some embodiments, be similar to any one or more of the embodiments, features, systems, devices, materials, methods and techniques described in the incorporated references. In addition, the embodiments, features, systems, devices, materials, methods and techniques described herein may, in certain embodiments, be applied to or used in connection with any one or more of the embodiments, features, systems, devices, materials, drugs (including photoreactive agents), methods and techniques disclosed in the above-mentioned incorporated references.

These and other changes can be made to the invention in light of the above-detailed description. In general, in the following claims, the terms used should not be construed to limit the invention to the specific embodiments disclosed in the specification and the claims, but should be construed to include all systems that operated in accordance with the claims.

What is claimed is:

1. A method of treating a target site of an individual, the method comprising:
    delivering a photoreactive agent to a target site of an individual, the target site having a visible network of spider veins;
    positioning at least one light emitter external to the individual and within optical range of the target site; and
    delivering light from the at least one light emitter, positioned external to the individual, towards the target site to activate the photoreactive agent to reduce or eliminate the visibility of the network of spider veins,
    wherein the photoreactive agent is talaporfin sodium.

2. The method of claim 1, wherein delivering the photoreactive agent comprises injecting the photoreactive agent directly into the network of spider veins.

3. The method of claim 1, further comprising: viewing a magnified image of at least a portion of the network of spider veins using a visualization device prior to delivering the photoreactive agent.

4. The method of claim 1, wherein delivering the light comprises delivering the light to a substantial portion of the network of spider veins to kill, to damage, to induce apoptosis in, or induce necrosis in the network of spider veins.

5. The method of claim 1, wherein delivering the light comprises illuminating a majority of the target site.

6. The method of claim 1, wherein delivering the light comprises delivering a sufficient amount of light to reduce a distance at which the network of spider veins is visually identifiable with a naked eye at least 0.5 meter.

7. The method of claim 1, further comprising:
    removing material from a mask of a patch that carries the at least one light emitter so as to form a window adjacent to the at least one light emitter; and
    positioning the mask adjacent to the target site such that the window is between the at least one light emitter and the target site.

8. The method of claim 7, wherein removing the material from the mask includes cutting the material from the mask.

9. The method of claim 7, further comprising: sizing the window based on an evaluation of the network of spider veins.

10. The method of claim 1, wherein delivering the light comprises providing a treatment field of light that has an outer boundary corresponding to an outer boundary of the network of spider veins.

11. The method of claim 1, further comprising: positioning an optical coupler between the at least one light emitter and the target site to increase an amount of light that reaches spider veins at the target site.

12. The method of claim 1, wherein delivering the light comprises providing a total light dose less than about 1000 Joules.

13. The method of claim 1, wherein delivering the light comprises providing a total light dose between about 5 Joules and about 40 Joules.

14. The method of claim 1, wherein delivering the light is performed about 1 minute to about 10 minutes after delivering the photoreactive agent to the target site.

15. A method of performing light treatment on a subject, comprising:
    sensitizing a target site with a photoreactive agent;
    positioning an external mask on the subject to define an outer boundary of the target site; and delivering light from a light emitter to tissue within the outer boundary of the target site sensitized with the photoreactive agent, while the mask substantially prevents light from the light emitter from reaching tissue outside the outer boundary of the target site, wherein the photoreactive agent is talaporfin sodium.

16. The method of claim 15, wherein positioning the external mask comprises spreading a non-transmissive substance on the subject.

17. The method of claim 16, wherein the non-transmissive substance is a flowable, optically opaque substance.

18. The method of claim 15, wherein positioning the external mask comprises tracing an outer boundary of a network of spider veins with a spreadable substance.

19. The method of claim 15, further comprising: positioning a patch, which includes the light emitter, on top of the mask.

20. The method of claim 15, wherein the target site includes a visible network of blood vessels.

21. The method of claim 15, wherein delivering the light causes a therapeutic alteration of the target site.

22. The method of claim 15, wherein delivering the light causes a cosmetic alteration of the target site without causing a therapeutic alteration of the target site.

* * * * *